United States Patent
Hwang et al.

(10) Patent No.: US 11,318,215 B2
(45) Date of Patent: *May 3, 2022

(54) COMPOSITION FOR GENE DELIVERY COMPRISING CHITOSAN AND LIQUID CRYSTAL FORMATION MATERIAL

(71) Applicant: CHONG KUN DANG PHARMACEUTICAL CORP., Seoul (KR)

(72) Inventors: Ho Young Hwang, Gyeonggi-do (KR); Ji Hye Hwang, Gyeonggi-do (KR); Young Nam Lee, Gyeonggi-do (KR); Sang Myoung Noh, Gyeonggi-do (KR); Min Hyo Ki, Gyeonggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/764,156

(22) PCT Filed: Feb. 28, 2014

(86) PCT No.: PCT/KR2014/001656
§ 371 (c)(1),
(2) Date: Jul. 28, 2015

(87) PCT Pub. No.: WO2014/133351
PCT Pub. Date: Sep. 4, 2014

(65) Prior Publication Data
US 2015/0374850 A1     Dec. 31, 2015

(30) Foreign Application Priority Data

Feb. 28, 2013 (KR) .................. 10-2013-0022333

(51) Int. Cl.
| | |
|---|---|
| *A61K 9/00* | (2006.01) |
| *A61K 47/00* | (2006.01) |
| *A61K 48/00* | (2006.01) |
| *A61K 9/19* | (2006.01) |
| *A61K 31/722* | (2006.01) |
| *A61K 9/127* | (2006.01) |
| *C12N 15/11* | (2006.01) |
| *A61K 9/14* | (2006.01) |
| *A61K 31/7088* | (2006.01) |
| *A61K 31/713* | (2006.01) |
| *A61K 47/14* | (2017.01) |
| *A61K 47/24* | (2006.01) |
| *A61K 47/26* | (2006.01) |
| *A61K 47/28* | (2006.01) |
| *A61K 47/36* | (2006.01) |
| *C12N 15/113* | (2010.01) |

(52) U.S. Cl.
CPC ........ *A61K 48/0041* (2013.01); *A61K 9/0019* (2013.01); *A61K 9/1274* (2013.01); *A61K 9/14* (2013.01); *A61K 9/19* (2013.01); *A61K 31/7088* (2013.01); *A61K 31/713* (2013.01); *A61K 31/722* (2013.01); *A61K 47/14* (2013.01); *A61K 47/24* (2013.01); *A61K 47/26* (2013.01); *A61K 47/28* (2013.01); *A61K 47/36* (2013.01); *C12N 15/111* (2013.01); *C12N 15/113* (2013.01); *C12N 2310/11* (2013.01); *C12N 2310/12* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 3,919,411 | A | * | 11/1975 | Glass ..................... A61K 39/39 424/213.1 |
| 7,361,640 | B2 | | 4/2008 | Huang et al. ................. 424/450 |
| 9,173,853 | B2 | | 11/2015 | Lee et al. ...................... 424/489 |
| 2003/0068277 | A1 | | 4/2003 | Vanbever et al. .............. 424/46 |
| 2003/0129240 | A1 | * | 7/2003 | Reeve .................. A61K 9/0014 424/486 |
| 2003/0212031 | A1 | | 11/2003 | Huang et al. ................. 435/458 |
| 2004/0022820 | A1 | * | 2/2004 | Anderson ............ A61K 9/1274 424/401 |
| 2007/0108405 | A1 | * | 5/2007 | Khoo ................... A61K 9/1075 252/299.01 |

(Continued)

FOREIGN PATENT DOCUMENTS

| | | | |
|---|---|---|---|
| GB | WO 06/077362 | * | 7/2006 |
| JP | H09-067273 | | 3/1997 |

(Continued)

OTHER PUBLICATIONS

Otake et al., Langmuir, 2006, 22: 4054-4059.*
Rengel et al., (Eur. J. Pharm, Sci., 2002, 14: 441-448.*
Libster et al., J. Colloid Interface Sci., 2011, 356: 375-386.*
Epstein, Gene Therapy, 2009, 16: 709-715.*
Salentinig et al., J. Colloid Interface Sci., 2008, 326: 211-220.*
Müller-Goyman, Eur. J. Pharm. Biopharm., 2004, 58: 343-356.*
Boyd et al., Int. J. Pharmaceutics, 2006, 309: 218-226.*
Svensson et al., J. Colloid Interface Sci., 2008, 325: 346-350.*

(Continued)

*Primary Examiner* — Ileana Popa
(74) *Attorney, Agent, or Firm* — Dentons US LLP; Stephanie Seidman (57) ABSTRACT

Disclosed herein is a composition for gene delivery which forms into liquid crystals in an aqueous fluid including chitosan and a liquid crystal formation material. The composition of the present invention including chitosan and a liquid crystal formation material improves the relatively low binding strength between chitosan and a gene, and also considerably increases the stability of a chitosan nanocomposite in blood serum, thereby performing highly efficient gene delivery and providing excellent stability, thus being useful as a gene therapeutic agent.

12 Claims, 2 Drawing Sheets

(56) References Cited

U.S. PATENT DOCUMENTS

| | | | |
|---|---|---|---|
| 2008/0085263 A1 | 4/2008 | Thuresson et al. | 424/85.7 |
| 2008/0131371 A1 | 6/2008 | Artursson et al. | 424/9.1 |
| 2008/0274176 A1 | 11/2008 | Johnsson et al. | 424/463 |
| 2009/0061007 A1 | 3/2009 | Tsukada et al. | 424/493 |
| 2010/0040694 A1 | 2/2010 | Nah et al. | 424/489 |
| 2010/0113559 A1 | 5/2010 | Park et al. | 514/44 A |
| 2011/0038941 A1* | 2/2011 | Lee | C12N 15/88 424/498 |
| 2012/0015026 A1 | 1/2012 | Francese et al. | 424/450 |
| 2013/0266641 A1 | 10/2013 | Choi et al. | 424/450 |
| 2014/0105968 A1 | 4/2014 | Takeuchi et al. | 424/450 |
| 2014/0206616 A1 | 7/2014 | Ko et al. | 514/11.7 |
| 2015/0050347 A1 | 2/2015 | Maurel | 424/489 |
| 2015/0110876 A1 | 4/2015 | Lee et al. | 424/489 |
| 2015/0265535 A1 | 9/2015 | Yu et al. | 424/400 |
| 2015/0290332 A1 | 10/2015 | Yoon et al. | A61K 47/24 |
| 2015/0297726 A1 | 10/2015 | Yoon et al. | 514/10.3 |
| 2015/0322023 A1 | 11/2015 | Lee et al. | 546/290 |
| 2016/0083354 A1 | 3/2016 | Lee et al. | 544/374 |
| 2016/0152988 A1 | 6/2016 | Merzouki et al. | 514/44 A |

FOREIGN PATENT DOCUMENTS

| | | |
|---|---|---|
| JP | 2000-516916 | 12/2000 |
| JP | 2003-001097 | 1/2003 |
| JP | 2008-501676 A | 1/2008 |
| JP | 2008-056611 A | 3/2008 |
| JP | 2008-528463 | 7/2008 |
| JP | 2010-503640 A | 2/2010 |
| JP | A 2010-515678 | 5/2010 |
| JP | 2011-500671 | 1/2011 |
| KR | Pub. No. 10-2004-0058199 | 7/2004 |
| KR | Pub. No. 10-2012-0013336 | 9/2010 |
| KR | Pat. No. 10-1308591 | 9/2013 |
| WO | WO 1998/047487 | 10/1998 |
| WO | WO 99/36089 | 7/1999 |
| WO | WO 2003/030941 | 2/2004 |
| WO | WO 2004/074314 | 9/2004 |
| WO | WO 2008/120736 | 10/2008 |
| WO | WO 2009/051451 | 4/2009 |
| WO | WO 2011/117334 | 9/2011 |
| WO | WO 2012/128417 | 9/2012 |
| WO | WO 2012/159215 | 11/2012 |
| WO | WO 2012/165468 | 12/2012 |
| WO | WO 2013/032207 | 3/2013 |

OTHER PUBLICATIONS

Wang et al., Drug Delivery, 2011, 18: 208-214.*
Yahgmur et al., Advances in Colloid and Interface Delivery, 2009, 147-148: 333-342.*
Pitto-Barry et al., Polym. Chem., 2014, 5: 3291-3297.*
Leong et al., J. Control. Rel., 1998, 53: 183-193.*
Gustafsson et al., Langmuir, 1997, 13: 6964-6971.*
Vicentini, Eur. J. Pharm. Biopharm., online Sep. 23, 2012, 83: 16-24.*
Dimitrov et al., Am. J. Clin. Nutr., 1996, 64: 329-335.*
Johnson et al., Langmuir, 2005, 21: 5159-5165.*
Gaemers et al., J. Am. Chem. Soc., 2001, 123: 12343-12352.*
Kaneko, Virology, 2000, 267: 8-16.*
Letter/Written Disclosure of the Information Disclosure Statement for the above-referenced application, mailed on Nov. 6, 2015, 2 pages.
"Molecular action of protamine on gene introduction by using positively charged liposome," The Journal of Japanese Biochemical Society 1P-689 [in Japanese language with English translation], 73(8):795, 5 pages (2001).
Chono et al., "An efficient and Low immunostimulatory nanoparticle formulation for systemic siRNA delivery to the tumor," Journal of Controlled Release 131:64-69 (2008).
Karmali, P. and D. Simberg, "Interactions of nanoparticles with plasma proteins:implication on clearance and toxicity of drug delivery systems," Expert Opinion DD 8(3):343-357 (2011).
Kumar et al., "Chitosan IFN-γ-pDNA Nanoparticle (CIN) Therapy for Allergic Asthma" Genetic Vaccines and Therapy 1(3):1-10 (2003).
Lappalainen et al., "Comparison of cell proliferation and toxicity assays using two cationic liposomes," Pharmaceutical Research 11(8):1127-1131 (1994).
Liu et al., "N-alkylated chitosan as a potential nonviral vector for gene transfection," Bioconjugate Chemistry 14(4):782-789 (2003).
Ljusberg-Wahren et al., "Enzymatic characterization of lipid-based drug delivery systems.," Int. J. Pharm 298(2):328-332 (2005).
Mansouri et al., "Chitosan-DNA nanoparticles as non-viral vectors in gene therapy: strategies to improve transfection efficacy," Eur J Pharm Biopharm 57(1): 1-8 (2004).
Mao et al. "Chitosan-based formulations for delivery of DNA and siRNA," Advanced Drug Delivery Reviews 62:12-27 (2010).
Prashanth et al., "Chitin/chitosan:modifications and their unlimited application potential—an overview," Trends in Food Science & Technology 18:117-131 (2007).
Rojanarata et al., "Chitosan-thiamine pyrophosphate as a novel carrier for siRNA delivery," Pharma. Res. 25(12):2807-2814 (2008).
Romano G., "Development of safer gene delivery systems to minimize the risk of insertional mutagenesis-related malignancies: a critical issue for the field of gene therapy," ISRN Oncology. Article ID 616310, 14 pages (2012).
Sah, H. and Y. Bahl, "Effects of aqeous phase composition upon protein destabilization at water/organic solvent interface," J. Control Release 106(1-2):51-61 (2005).
Safinya et al., "Cationic liposome-DNA complexes: from liquid crystal science to gene delivery applications," Philos Trans A Math Phys Eng Sci 364(1847):2573-2596 (2006).
Saminathan et al., "Polyamine structural effects on the induction and stabilization of liquid crystalline DNA: potential applications to DNA packaging, gene therapy and polyamine therapeutics," Nucleic Acids Res. 30(17):3722-3731 (2002).
Tanaka, K. and K. Miyajima, "The freeze-drying of liposome with saccharides and their protection mechanism," Membrane 18(3):156-163 (1993) [in Japanese language with English language abstract].
Ungar et al., "Giant supramolecular liquid crystal lattice," Science. 299(5610):1208-1211 (2003).
Wang et al., "Delivery of siRNA Therapeutics:Barriers and carriers," The AAPS Journal 12(4):492-503 (2010).
Welz et al., "Nuclear transport of oligonucleotides in HepG2-cells mediated by protamine sulfate and negatively charged liposomes." Pharm Res. 17(10):1206-1211 (2000).
International Search Report and Written Opinion, dated Mar. 26, 2013, in connection with International Patent Application No. PCT/KR2012/009443, 6 pages.
International Preliminary Report on Patentability, dated May 13, 2014, in connection with International Patent Application No. PCT/KR2012/009443, 4 pages.
International Search Report and Written Opinion, dated May 28, 2014, in connection with corresponding International Patent Application No. PCT/KR2014/001656, 9 pages.
Office Action, dated May 12, 2015, in connection with Japanese Patent Application No. 2014-540950 [English translation with original document in Japanese], 6 pages.
Extended European Search Report, dated Jun. 15, 2015, in connection with European Patent Application No. 12847217.2, 5 pages.
Notice of Allowance, dated Jun. 23, 2015, in connection with U.S. Appl. No. 14/357,375, 12 pages.
Supplemental Notice of Allowability, dated Aug. 6, 2015, in connection with U.S. Appl. No. 14/357,375, 2 pages.
Response to Extended European Search Report, dated Aug. 24, 2015, in connection with European Patent Application No. 12847217.2, 9 pages.
International Preliminary Report on Patentability, dated Sep. 1, 2015, in connection with International Patent Application No. PCT/KR2014/001656, 6 pages.

(56) References Cited

OTHER PUBLICATIONS

Letter/Written Disclosure of the Supplemental Information Disclosure Statement for the above-referenced application, filed herewith on Sep. 7, 2016, 2 pages.
English language abstract of Japanese Patent Publication No. JP 2003-001097, accessed from Espacenet on Aug. 30, 2016, 5 pages.
Lasic et al., "Transmembrane gradient driven phase transitions within vesicles: lessons for drug delivery," Biochimica et Biophysica Acta 1239:145-156 (1995).
Machine-generated English translation of WO 2012/128417, published Sep. 27, 2012, PatentScope, World Intellectual Property Organization, 6 pages.
Machine-generated English translation of WO 2012/165468, published Dec. 6, 2012, PatentScope, World Intellectual Property Organization, 16 pages.
Nema et al., "Excipients and their use in injectable products," PDA J Pharm Sci Technol 51(4):166-171 (1997).
Office Action, dated Aug. 23, 2016, in connection with Japanese Patent Application No. 2015-560102 [English translation and original document in Japanese], 7 pages.
Letter/Written Disclosure of the Supplemental Information Disclosure Statement for the above-referenced application, filed herewith on Apr. 27, 2017, 2 pages.
Extended European Search Report, dated Sep. 16, 2016, in connection with corresponding European Patent Application No. 14756578.2, 8 pages.
Response, submitted Mar. 29, 2017, to Extended European Search Report, dated Sep. 16, 2016, in connection with corresponding European Patent Application No. 14756578.2, 15 pages.
U.S. Appl. No. 14/241,696, filed Feb. 27, 2014, 2014/0206616, Jul. 24, 2014.
U.S. Appl. No. 14/440,058, filed Apr. 30, 2015, 2015/0265535, Sep. 24, 2015.
U.S. Appl. No. 14/440,059, filed Apr. 30, 2015, 2015/0290332, Oct. 15, 2015.
U.S. Appl. No. 14/440,060, filed Apr. 30, 2015, 2015/0297726, Oct. 22, 2015.
U.S. Appl. No. 14/651,211, filed Jun. 10, 2015, 2015/0322023, Nov. 12, 2015.
U.S. Appl. No. 14/785,812, filed Oct. 20, 2015, 2016/0083354, Mar. 24, 2016.
Letter/Written Disclosure of the Supplemental Information Disclosure Statement for the above-referenced application, filed herewith on May 3, 2018, 2 pages.
Hoekstra et al., "Gene delivery by cationic lipids: in and out of an endosome," Biochemical Society Transactions 35(part 1):68-71 (2007).
Karami, Z and M. Hamidi, "Cubosomes: remarkable drug delivery potential," Drug Discovery Today 21(5): 789-801 (2016).
Ki et al., "A new injectable liquid crystal system for one month delivery of leuprolide," Journal of Controlled Release 185:62-70 (2014).
Kim, H. and C. Leal, "Cuboplexes: Topologically Active siRNA Delivery," ACS Nano 9(10):10214-10226 (2015).
Landry et al., "Progress in RNAi-mediated Molecular Therapy of Acute and Chronic Myeloid Leukemia," Molecular Therapy—Nucleic Acids 4:e240; doi: 10.1038/mtna.2015.13, 23 pages (2015).
Communication under Rule 71(3) EPC (Intention to Grant), dated Mar. 23, 2018, in connection with corresponding European Patent Application No. 14 756 578.2, 39 pages.
Letter/Written Disclosure of the Supplemental Information Disclosure Statement for the above-referenced application, filed herewith on Sep. 10, 2019, 2 pages.
Chan et al., "Chitosan-Induced Perturbation of Dipalmitoyl-sn-glycero-3-phosphocholine Membrane Bilayer," Langmuir 17(12):3749-3756 (2001).
Machine-generated English translation of JP 2000-516916, published Dec. 19, 2000, 25 pages.
Machine-generated English translation of JP H09-067273, published Mar. 11, 1997, 25 pages.
Response, filed Jan. 23, 2017, to Office Action, dated Aug. 23, 2016, in connection with corresponding Japanese Patent Application No. 2015-560102 [machine-generated English translation and document in Japanese, as accessed from <URL:j-platpat.inpit.go.jp/ on May 29, 2019], 30 pages.
Decision to Grant, dated Feb. 21, 2017, in connection with corresponding Japanese Patent Application No. 2015-560102 [machine-generated English translation and document in Japanese, as accessed from <URL:j-platpat.inpit.go.jp/ on May 29, 2019], 9 pages.

\* cited by examiner

COMPOSITION FOR GENE DELIVERY COMPRISING CHITOSAN AND LIQUID CRYSTAL FORMATION MATERIAL

RELATED APPLICATIONS

This application is the U.S. National Stage of International Application. No. PCT/KR2014/001656, filed 28 Feb. 2014, which claims benefit of priority to Korean Patent Application KR 10-2013-0022333, filed 28 Feb. 2013, the specification of which is incorporated by reference herein.

TECHNICAL FIELD

The present invention relates generally to a composition for gene delivery which forms into liquid crystals in an aqueous fluid including chitosan and a liquid crystal formation material.

BACKGROUND ART

Gene therapy aiming at treatment of diseases has been continuously studied and commercialization of the study results of the gene therapy has been under continued effort. A gene is a material including nucleotides and nucleic acids which are polymers of nucleotides, and carries a strong negative charge due to phosphate groups carried on by each monomer of the nucleic acids. The gene therapy technology, as compared to the conventional chemotherapy technology, works at a level of DNA or RNA. However, genes can be easily decomposed by nucleases and have a relatively short life span in cells or living organisms and thus the study of the technology related to "gene transfection delivery" is a prerequisite.

Gene transfection delivery may be divided according to the use of viruses, e.g., a viral vector and a non-viral vector, and each has its own merits and demerits.

The viral vector employs an intrinsic cellular invasion of a virus to cause inflammation in human cells and has thus been considered to provide a more efficient gene delivery mechanism in cells than that of a non-viral vector. However, the viral vector has not yet resolved difficulty in long term administration due to immune responses and has not eliminated the possibility of the replication of the pathogenic virus (ISRN Oncology, 2012, Article ID 616310, 14 pages).

In order to remedy the above shortcomings and the danger of viral vectors, research has been focused on the development of gene delivery via a non-viral vector. Over the viral vector, the non-viral vector has advantages that it has no risk of inflammation, no limitation on the size of a gene for delivery and is less problematic in terms of immunogenicity in the body, and convenient for multiple doses. The non-viral vector may be divided into a positively charged lipid and a positively charged polymer. The binding between a non-viral vector and a negatively charged gene for delivery is facilitated by electrostatic attraction. Therefore, the non-viral vector has the advantage that it can easily provide a composite by a physical mixing of the negatively charged gene for delivery and the positively charged vector.

Korean Patent Application Publication No. 10-2012-0078661 discloses a gene delivery method using a complex in which a synthetic cationic lipid forms an ionic bond with the gene. In particular, it relates to the formation of a non-covalent ionic bond by adding a gene to a solution consisting of at least one cationic lipid and various surfactants. The cationic lipid in the above method may have cytotoxicity, and the lipid synthesized thereof is a material requiring high purity purification, and thus raises a problem for a large scale production due to the difficulty in quality control. Additionally, the method has the disadvantage that it has relatively low stability during storage and distribution thus making it difficult in terms of commercialization. Accordingly, the method of the present invention is different from the above method in that it provides a method for gene delivery with high stability by forming a liquid crystal by using a mixture of injectable lipids unlike the synthesized cationic lipid in the above Korean Patent Application.

U.S. Patent Application Publication No. 2011-0038941 describes a method for manufacturing an oligonucleotide-lipid nanoparticle consisting of an oligonucleotide, a lipid, and a complexation agent, which includes 1) mixing a lipid, a complexing agent and a cationic polymer in a water miscible organic solvent; 2) dissolving the oligonucleotide in an aqueous buffer; and, 3) injecting the first mixture prepared in 1) into the second mixture prepared in 2), or mixing the first mixture prepared in 1) and the second mixture prepared in 2) under pressure to form a third mixture; and 4) removing the organic solvent from the third mixture prepared in 3). The above method is disadvantageous because of the difficulty in quality control and also that it requires a special machine during the manufacturing process. In addition, due to the difficulty in large scale production, the method is difficult to apply in industry. Although the method discloses protamine and chitosan while claiming a wide scope of materials it fails to describe exemplary embodiments of the compositions for gene delivery including chitosan or the effects what are sought to be protected. Besides, the method relates to a method of manufacturing nanoparticles which requires a mixing process under specific environmental conditions and removing of an organic solvent, and thus differs from that of the present invention.

A liquid crystal is a state of matter intermediate between solid and liquid. Although the molecular configuration of the liquid crystal is not strictly regular as in the case of a solid crystal, it forms a crystal in a relatively regular state when there is a phase transition from a solid, unlike the normal liquid which becomes amorphous. Thus, a liquid crystal is called meso-phase matter.

Korean Patent Application Publication No. 10-2012-0013336 discloses a gene delivery system comprising a liquid crystal nanoparticle composed of a diacyl lipid enclosing an aqueous cavity and a gene contained within the aqueous cavity. This system is described to not produce lactic acid or glycolic acid degradation products, thus not causing pain or inflammation in injection sites, and allows the sustained release of a pharmacologically active substance in vivo for four weeks. However, diacyl lipid, the core constituent of the above preparation material, has not been guaranteed to be safe and thus it raises a problem that it cannot be generally used as an excipient of a pharmaceutical drug. Additionally, the system is not advantageous in that it requires the use of an organic solvent which lowers the activity of a few pharmacologically active materials (H. Ljusberg-Wahre, F. S. Nielse, 298, 328-332 (2005); H. Sah, Y. bahl, Journal of Controlled Release 106, 51-61(2005)).

In manufacturing a gene delivery complex, chitosan can be a good candidate for a non-viral delivery vector because it has an excellent biocompatibility and is a natural cationic material suitable for large scale production. In particular, chitosan can be decomposed into an amino sugar by lysozyme when it enters a living body, and is a safe polymer material whose LD50 in rats is known to be 16 g/kg (Trends in Food Science & Technology, 2007; 18: 117-131).

Chitosan is a strong candidate for a non-viral vector for delivery of a gene into a cell because it can form an ionic bond with a gene. However, its cationic charge becomes weak in a physiological pH (pH 7-7.4) and thus its binding strength with a gene becomes deteriorated. As a result, chitosan cannot maintain a complex with a gene under the above physiological pH condition and becomes released, thus drastically reducing its effect on gene delivery.

A nanocomposite simply consisting of chitosan, a gene and thiamine pyrophosphate can improve in vitro gene delivery. However, in an in vivo condition unlike in an in vitro condition, a chitosan complex may not perform excellent gene delivery due to the presence of various serum proteins and cell exudates. This is because the chitosan nanocomposite, once introduced into a living body, precipitates by coagulating with serum proteins in vivo and thereby fails to perform gene delivery. Accordingly, due to its in vivo incompatibility, the conventional chitosan composite has not been successful in its commercialization as a gene delivery vector (Expert Opinion on Drug Delivery, 2011; 8: 343-357).

As such, in order for chitosan to be applicable in a human body as a gene delivery vector, it is essential that the chitosan nanocomposite have the required gene delivery capability at a physiological pH, and also maintain the stability as a nanocomposite without causing coagulation even when introduced into a living body.

Nevertheless, regarding the gene delivery using chitosan, there has been no report on the establishment of a sure technology which enables to maintain stability of the nanocomposite within blood serum without showing any toxicity while effectively performing gene delivery in a living body, thus necessitating the need for the development of a gene delivery vector using chitosan.

PATENT DOCUMENTS

Korean Patent No. 10-2012-0078661
U.S. Patent Application Publication No. 2011-0038941

NON-PATENT DOCUMENTS

Development of Safer Gene Delivery Systems to Minimize the Risk of Insertional Mutagenesis-Related Malignancies: A Critical Issue for the Field of Gene Therapy (ISRN Oncology, 2012, Article ID 616310, 14p)
Enzymatic characterization of lipid-based drug delivery systems (H. Ljusberg-Wahre, F. S. Nielse, Int J Pharm. 2005; 298:328-332(2005))
Effects of aqueous phase composition upon protein destabilization at water/organic solvent interface (H. Sah, Y. Bahl, Journal of Controlled Release 106, 51-61(2005)).
Chitin/chitosan: modifications and their unlimited application potential—an overview (K. V. Harish Prashanth, R. N. Tharanathan, Trends in Food Science & Technology, March 2007, Pages 117-131)
Interactions of nanoparticles with plasma proteins: implication on clearance and toxicity of drug delivery systems (Priya Prakash Karmalil & Dmitri Simberg, Pages 343-357)

DISCLOSURE OF INVENTION

Technical Problem

Accordingly, the present invention has been made keeping in mind the above problems occurring in the prior art, and an object of the present invention is to provide a composition for delivery of a gene including a liquid crystal formation material and chitosan.

Another object of the present invention is to provide a nanocomposite including a liquid crystal formation material, chitosan, and a gene.

Solution to Problem

In order to accomplish the above objects, the present invention provides a composition for gene delivery which forms into liquid crystals in an aqueous fluid including a liquid crystal formation material, phospholipid, a liquid crystal hardener, and chitosan.

The composition of the present invention for gene delivery has high efficiency gene delivery capability and excellent stability by considerably improving the relatively low binding strength between chitosan and a gene, and drastically improving the stability of chitosan nanocomposites in blood serum, thus being useful as a gene therapeutic agent.

More specifically, the liquid crystal formation material, phospholipid and a liquid crystal hardener of the present invention can form liquid crystals in the presence of an aqueous solution. The thus formed liquid crystals form stable nanocomposites along with chitosan and genes, thereby considerably enhancing the gene delivery capability, and also due to their stability, the nanocomposites can be maintained in a uniform state for a long period of time.

The "liquid crystal formation material" of the present invention is a material which forms liquid crystals having a non-lamellar structure. It may be selected from the group consisting of sorbitan unsaturated fatty acid ester, monoacyl glycerol, diacyl glycerol, and a combination thereof.

In addition, the liquid crystal formation material may be a sorbitan unsaturated fatty acid ester which has at least two hydroxyl (—OH) groups in the polar head group. The sorbitan unsaturated fatty acid ester is a compound represented by Formula 1 below, wherein sorbitan monoester is R1=R2=OH, R3=R, and sorbitan diester is R1=OH, R2=R3=R, wherein R is an $C_4$-$C_{40}$ alkyl ester group having at least one double bond.

[Formula 1]

More specifically, the sorbitan unsaturated fatty acid ester of the present invention may be obtained from vegetable oils, animal fat and animal oils, whale oil, and fish oils. Preferred examples of the vegetable oil include cacao butter, borage oil, rice bran oil, green tea oil, soybean oil, hempseed oil, sesame oil, cherry seed oil, rape seed oil, poppy seed oil, pumpkin seed oil, grape seed oil, apricot kernel oil, coconut oil, camellia oil, evening primrose oil, rape oil, sunflower oil, canola oil, pine nut oil, walnut oil, hazelnut oil, avocado oil, almond oil, peanut oil, jojoba oil, palm oil, castor oil, olive oil, corn oil, sesame oil, cotton seed oil, safflower seed oil, borage oil and primrose oil. Preferred examples of animal fats and oils may include, milk fat, beef tallow, mammalian oil, reptile oil, and bird oil, and preferably, at least one selected from the group consisting of sorbitan monoester, sorbitan sesquiester, sorbitan diester, and a combination thereof, which can be obtained from whale oil and fish oil.

Preferably, the sorbitan unsaturated fatty acid ester may be sorbitan monooleate, sorbitan monolinoleate, sorbitan monopalmitoleate, sorbitan monomyristoleate, and a combination thereof, wherein one fatty acid group is ester-bonded to sorbitan.

The sorbitan sesquiester may be at least one selected from the group consisting of sorbitan sesquioleate, sorbitan sesquilinoleate, sorbitan sesquipalmitoleate, sorbitan sesquimyristoleate, and a combination thereof, wherein at least 1.5 fatty acid groups are ester-bonded to sorbitan.

The sorbitan diester may be at least one selected from the group consisting of sorbitan dioleate, sorbitan dilinoleate, sorbitan dipalmitoleate, sorbitan dimyristoleate, and a combination thereof, wherein at least 2 fatty acid groups are ester-bonded to sorbitan.

In addition, monoacyl glycerol, another form of a liquid crystal formation material in the present invention, is a compound where one fatty acid group is ester-bonded to a polar head group consisting of glycerine, and diacyl glycerol is a compound where two fatty acid groups, which may be the same or different, ester-bonded to a polar head group consisting of glycerine. The fatty acid groups, which are ester-bond to monoacyl glycerol and diacyl glycerol of the present invention, have about 4 to about 30 carbon atoms, which may be the same or different, and may be independently saturated or unsaturated. More specifically, the fatty acid groups may be at least one selected from the group consisting of palmitic acid, palmitoleic acid, lauric acid, butyric acid, valeric acid, caproic acid, enanthic acid, caprylic acid, pelargonic acid, capric acid, myristic acid, myristoleic acid, stearic acid, arachidic acid, bebenic acid, lignoceric acid, cerotic acid, linolenic acid, alpha-linolenic acid (ALA), eicosapentaenoic acid (EPA), docosahexaenoic acid (DHA), linoleic acid (LA), gamma-linoleic acid (GLA), dihomo gamma-linoleic acid (DGLA), arachidonic acid (AA), oleic acid, Vaccenic acid, elaidic acid, eicosanoic acid, erucic acid, nervonic acid, and a combination thereof.

More specifically, the monoacyl glycerol of the present invention may be at least one selected from the group consisting of glycerol monobutyrate, glycerol monobehenate, glycerol monocaprylate, glycerol monolaurate, glycerol monomethacrylate, glycerol monopalmitate, glycerol monostearate, glycerol monooleate, glycerol monolinoleate, glycerol monoarchidate, glycerol monoarchidonate, glycerol monoerucate, and a combination thereof.

Preferably, glycerol monooleate (GMO) represented by Formula 2 below may be used.

[Formula 2]

GMO

Additionally, the diacyl glycerol of the present invention may be at least one selected from the group consisting of glycerol dibehenate, glycol dilaurate, glycerol dimethacrylate, glycerol dipalmitate, glycerol distearate, glycerol dioleate, glycerol dilinoleate, glycerol dierucate, glycerol dimyristate, glycerol diricinoleate, glycerol dipalmitoleate, and a combination thereof.

Preferably, glycerol dioleate (GDO) represented by Formula 3 below may be used.

[Formula 3]

GDO

"Phospholipids" of present invention are essential for the construction of lamellar structures, such as liposomes, in conventional techniques, but, cannot form a non-lamellar phase structure, such as a liquid crystal, by themselves. However, phospholipids can participate in the liquid crystal formation material-driven formation of non-lamellar phase structures, serving to stabilize the resulting liquid crystals.

The phospholipid useful in the present invention is derived from plants or animals, and preferably contains a saturated or unsaturated alkyl ester group of 4 to 30 carbon atoms with a polar head. The phospholipid may be selected more than one from among phosphatidylcholine, phosphatidylethanolamine, phosphatidylserine, phosphatidylglycerine, phosphatidylinositol, phosphatidic acid, sphingomyelin, and a combination thereof according to the structure of the polar head. The alkyl ester group to be bound to the phospholipid may be a saturated fatty acid ester such as mono- and dipalmitoyl, mono- and dimyristoyl, mono- and dilauryl, mono- and distearyl, etc., or an unsaturated fatty acid ester such as mono- and dilinoleyl, mono- and dioleyl, mono- and dipalmitoleyl, mono- and dimyristoleyl, etc., and also, may be in a form where both the saturated fatty acid ester and the unsaturated fatty acid ester may coexist.

In a preferred embodiment of the present invention, the phospholipid may be provided as a composition for gene delivery selected from the group consisting of phosphatidylcholine, phosphatidylethanolamine, phosphatidylserine, phosphatidylglycerine, phosphatidylinositol, phosphatidic acid, sphingomyelin, and a combination thereof.

The "liquid crystal hardener" of the present invention cannot form a non-lamellar structure, unlike the liquid crystal formation material, nor a lamellar structure such as liposome unlike phospholipids, by itself. However, the liquid crystal hardener contributes to the liquid crystal formation material-driven formation of non-lamellar phase structures by increasing the curvature of the non-lamellar structures to enhance the ordered co-existence of oil and water. In the interests of this function, the liquid crystal hardener is advantageously required to have a highly limited polar moiety and a bulky non-polar moiety inside its molecular structure.

In practice, however, biocompatible substance which are injectable into the body can be selected as the liquid crystal hardener of the present invention only via direct and repeated experiments, especially. As a result, liquid crystal hardeners suitable for the composition of the present invention has molecular structures which are different from one another and thus cannot be elucidated as having only one molecular structure. The common structural feature deduced by observation of all of the liquid crystal hardeners identified is that they are free of ionizable groups, such as carboxyl and amine groups, and have hydrophobic moieties comprising a bulky triacyl group with 15 to 40 carbon atoms or carbon ring structure.

Preferred examples of the liquid crystal hardener of the present invention may be free of ionizable groups, such as carboxyl and amine groups, and have at most one hydroxyl and ester group as a weak polar head, with hydrophobic moieties including a bulky triacyl group with 20 to 40 carbon atoms or carbon ring structure. Examples of the liquid crystal hardener of the present invention may include, but are not limited to, triglyceride, retinyl palmitate, tocopherol acetate, cholesterol, benzyl benzoate, ubiquinone, and a combination thereof.

In an exemplary embodiment of the present invention, the composition for gene delivery may include a liquid crystal hardener, which is at least one selected from the group consisting of triglyceride, retinyl palmitate, tocopherol acetate, cholesterol, benzyl benzoate, ubiquinone, and a combination thereof.

The liquid crystal may be formed by adding a surfactant in addition to the liquid crystal formation material, the phospholipid and the liquid crystal hardener. Preferably, the surfactants to be additionally added may be polysorbate 20, polysorbate 40, polysorbate 60, polysorbate 65, polysorbate 80, which are polyoxyethylene higher aliphatic alcohols, and more preferably polysorbate 80.

The "chitosan" of the present invention is a very safe cationic polysaccharide having a structure of (1->4) 2-amino-2-deoxy-β-D-glucan present in nature. Chitosan is a form of a polymer forming a free amine group by deacetylation of chitin obtained from natural Crustacea. In particular, the chitosan has a molecular weight of 1-500 kDa, has more than 50% of free amine groups, preferably has a molecular weight of 150-400 kDa, has more than 80% of free amine groups, but is not limited thereto.

In terms of solubilization of chitosan, water-soluble chitosan, water-insoluble chitosan, and chitosan derivatives with modified molecular structures may be included, preferably water-soluble chitosan.

The water-soluble chitosans may be one selected from the group consisting of chitosan HCl, chitosan acetate, chitosan glutamate, and chitosan lactate. The water-soluble chitosan is soluble in water because the amine groups in the water-soluble chitosans form salts with an acidic material such as HCl or acetic acid, glutamic acid, lactic acid, in an equivalent ratio. The water-soluble chitosan is advantageous in that it can eliminate bacteria or other impurities during the process of injection preparation.

In an exemplary embodiment of the present invention, the composition for gene delivery may further include a gene.

The gene may be a nucleotides and a nucleic acid which is a polymer of nucleotides, at least one selected from the group consisting of single-stranded or double-stranded deoxyribonucleic acid (DNA), single-stranded or double-stranded ribonucleic acid (RNA), plasmid (type) DNA, single-stranded or double-stranded small interfering RNA (siRNA), antisenese oligonucleotide, ribozyme, catalytic RNA and nucleotides. Preferably, the gene may be at least one selected from the group consisting of plasmid (type) DNA, single-stranded or double-stranded siRNA and antisenese oligonucleotide. Here, the gene may be a genetic drug, and the genetic drug refers to a gene which has efficacy for the treatment or prevention of at least one disease.

In an exemplary embodiment of the present invention, the composition for gene delivery may further include a dispersant.

"Dispersant" is a type of a surfactant having the opposite properties of hydrophobicity and hydrophilicity within a molecule, capable of uniformly dispersing organic and inorganic micro particles, which are difficult to disperse in a liquid, and preventing precipitation or agglutination of the particles, thereby maintaining a stable composition.

The dispersant to be used in the present invention may be in the form of an oligomer greater than 15-mer or a polymer, preferably, one selected from the group consisting of poloxamer, polyvinylalcohol, D-alpha-tocopherol polyethylene glycol succinate, polyethylene glycol-glyceryl monooleate, hydrophobically modified starch, and a combination thereof, more preferably, one selected from poloxamer, D-alpha-tocopherol polyethylene glycol succinate, and a combination thereof.

In an exemplary embodiment of the present invention, the composition for gene delivery may further include thiamine pyrophosphate or its pharmaceutically acceptable salts thereof.

The thiamine pyrophosphate is a safe material present in an active form of vitamin B1 being formed in the body when vitamin B1 is administered into the body. Furthermore, it has both cations and anions structurally within the compound thus capable of compensating the relatively weak bond between chitosan and a gene.

In an exemplary embodiment of the present invention, the composition for gene delivery may further include protamine or its pharmaceutically acceptable salts thereof.

Protamine is a natural cationic protein having plenty of arginine and has been used as an excipient of pharmaceutical drugs. Furthermore, protamine is a material predominantly present in animal testis, particularly in fish sperm nuclei such as salmon, and is known to be involved in expression of genetic information as in histone via association or dissociation with DNA. The molecular weight of protamine is about 4,000-10,000, where at least 70% of the constituents are present in the form of arginine, but is not limited thereto. In particular, the protamine salt of the present invention may include salts by an acidic material such as hydrochloride or sulfate.

Protamine is water-soluble even when it does not form a salt, and the salt type is also soluble in water. Therefore, any type of protamine may be used as a component of the composition for gene delivery of the present invention.

In an exemplary embodiment of the present invention, the composition for gene delivery may further include sodium lauryl sulfate.

Sodium lauryl sulfate is a representative anionic surfactant having a chemical formula of $CH_3(CH_2)_{10}CH_2OSO_3Na$. It is a white or light yellow crystal and consists of a mixture of sodium alkylsulfate. Additionally, it is used to uniformly disperse solids or liquids which are not miscible with each other in a liquid, and can prevent precipitation or agglutination of the particles in the composition of the present invention. In particular, sodium lauryl sulfate may serve to control the formulation type of the composition for gene delivery according to its content in the composition.

In an exemplary embodiment of the present invention, the composition for gene delivery may further include a saccharide, which may be at least one selected from the group consisting of mannose, glucose, fructose, arabinose, mannitol, sorbitol, sucrose, trehalose, maltose, lactose, cellobiose, isomaltose, dextran, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin and sulfobutylether β-cyclodextrin.

In an exemplary embodiment of the present invention, the composition for gene delivery may further include a pharmaceutical additive selected from the group consisting of a stabilizing agent, a buffer, a preservative, an analgesic agent and a tonicity agent.

The stabilizing agent may include an antioxidant, a reducing agent, and a chelator, etc. The buffer may include an organic or inorganic salt, etc., for pH control. The preservative may include an antiseptic component such as methyl ρ-Hydroxybenzoate, ethyl ρ-Hydroxybenzoate, propyl ρ-Hydroxybenzoate, butyl ρ-Hydroxybenzoate, chlorobutanol, benzalkonium chloride, benzethonium chloride, phenol, cresol, chlorocresol, and benzyl alcohol. The analgesic agent may include a local analgesic component such as benzyl alcohol and chlorobutanol. The tonicity agent may include saccharides and inorganic salts, etc., for osmotic control.

In an exemplary embodiment of the present invention, the composition for gene delivery may further include a formed nanocomposite. The nanocomposite may be formed by mixing a liquid crystal including liquid crystal formation material, phospholipid, a liquid crystal hardener, and chitosan, a gene. The size of the nanocomposite may be in the range of 10-500 nm, more preferably 10-300 nm, most preferably 50-300 nm, 100-300 nm, 150-300 nm, and 200-300 nm. The structure of the nanocomposite may be such that chitosan is present on the surface, preferably a structure where chitosan is coated on the surface.

In an exemplary embodiment of the present invention, the composition for gene delivery may include a solution containing liquid crystals, and a solution containing chitosan or a salt thereof.

The liquid crystals may include a liquid crystal formation material, phospholipid, a liquid crystal hardener, and within the scope of not departing the purpose of the present invention, may further include a material such as a surfactant.

In an exemplary embodiment, the present invention provides a lyophilized preparation of the composition for gene delivery, which includes a liquid crystal formation material, phospholipid, a liquid crystal hardener, chitosan or its salts.

Preferably, the lyophilized preparation may further include an excipient for lyophilization, and preferably, the excipient for lyophilization may be sugar alcohol or a saccharide, more preferably a saccharide.

Preferably, the sugar alcohol may be mannitol, erythritol, inositol, sorbitol. Preferably, the saccharide may be at least one selected from the group consisting of mannose, glucose, fructose, arabinose, mannitol, sorbitol, sucrose, trehalose, maltose, lactose, cellobiose, isomaltose, dextran, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin and sulfobutylether β-cyclodextrin, more preferably trehalose or glucose.

Preferred examples of the lyophilized preparation may include a pH adjuster, an antioxidant, an antiseptic, an osmotic pressure adjuster, etc.

Additionally, the lyophilized preparation of the present invention may be manufactured using a conventional lyophilization method in the related art, and rehydration after the lyophilization can attain an appropriate characteristic for reconstitution for achieving the purpose for gene delivery. That is, the composition for gene delivery of the present invention before lyophilization may be reconstructed via an easy redissolution by randomly adding any suitable solution (a redissolved solution). Examples of the redissolved solution may include water for injection, saline solution, other general infusion solution (e.g., glucose, amino acid infusion solution), etc., but is not limited thereto.

The rehydrated solution of the lyophilized preparation may be administered parenterally via an intravenous injection, an intramuscular injection, a subcutaneous injection, an intrauterine injection, a cerebrovascular injection, etc.

The composition of the present invention including the above mentioned components may be manufactured as described hereunder, but is not limited thereto.

The manufacturing method may include: 1) preparing a pre-complex by mixing a gene, sodium lauryl sulfate or thiamine pyrophosphate and protamine, and water-soluble chitosan in water; and 2) adding a solution where liquid crystals are dispersed therein and forming a final liquid nanocomposite. The nanocomposite formed therein may have a size from 10 to 500 nm to meet the required particle size for its introduction into a cell, preferably from 10 to 300 nm, more preferably from 50 to 300 nm, from 100 to 300 nm, from 150 to 300 nm, and from 200 to 300 nm.

The pre-complex of a gene of the present invention may be prepared by mixing a gene, sodium lauryl sulfate or thiamine pyrophosphate and protamine, and water-soluble chitosan and agitating the mixture thereafter, preferably, by mixing the gene and water-soluble chitosan in a weight ratio of 1:0.3-20. Sodium lauryl sulfate, thiamine pyrophosphate, protamine may be selectively included in the pre-complex. Preferably, the gene and sodium lauryl sulfate may be mixed in 1:1 weight ratio, the gene and thiamine pyrophosphate in 1:1-6 weight ratio, and the gene and protamine in 1:0.6 weight ratio, and then respectively agitated thereafter.

In the present invention, the solution where liquid crystals are dispersed may be formed by mixing a liquid crystal formation material, phospholipid, and a liquid crystal hardener, and agitating the mixture thereafter. More specifically, a lipid solution may be formed by agitating the mixture of a liquid crystal formation material, phospholipid, and a liquid crystal hardener at room temperature, and it may be uniformly prepared by adding a dispersant to the lipid solution prepared therefrom. In an exemplary embodiment, the solution where liquid crystals are dispersed may be prepared by mixing the liquid crystal formation material, phospholipid, and the liquid crystal hardener in a weight ratio of 0.20-1:1-1.5:0.05-0.2.

In the present invention, the solution where the gene pre-complex and liquid crystals are dispersed may be mixed and filtrated to thereby form a final liquid nanocomposite, and the thus prepared nanocomposite may be in a form where chitosan is coated thereon.

The lyophilized preparation of the present invention may be prepared by adding a sugar alcohol or a saccharide, preferably saccharide, as an excipient, to the finally prepared liquid nanocomposite, and mixing then lyophilizing the mixture thereafter. The saccharide may be in the form of a 20-40% solution, preferably 30% solution, and may be solidified at between −50 and −80° C., preferably, at −70° C.

In an aspect of the present invention, there is provided a nanocomposite including the composition for gene delivery. The nanocomposite may be used as a gene therapeutic agent, so that chitosan can be present on the surface of the nanocomposite and serve to coat the liquid crystals and the gene. The gene therapeutic agent is a suitable administration route for mammals including humans, for example, injections, transpulmonary, nasal, oral, and rectal administrations. Preferably, it may be administered via intravenous, intramuscular, subcutaneous, intrauterine, cerebrovascular injections, and may be directly administered onto particular tissues and organs and cancerous tissues as necessary.

In the present invention, the daily dosage of the gene therapeutic agent may be controlled in the range of 1 mg/kg-10 mg/kg. The optimum dosage to be administered can be easily determined by one of ordinary skill in the art, and may be adjusted depending on the type of the disease, the severity of the disease; the content of active ingredients and other components, types of formulations; age, body weight, health conditions, sex, age, and dietary habits of a subject; duration of administration, administration route, length of treatment, and the combination of administered drugs.

Advantageous Effects of Invention

The composition of the present invention including chitosan and a liquid crystal formation material can improve the relatively low binding strength between chitosan and a gene, and also considerably increases the stability of a chitosan nanocomposite in blood serum, thereby performing highly efficient gene delivery and excellent stability, thus being useful as a gene therapeutic agent.

MODE FOR THE INVENTION

Hereinafter, exemplary embodiments of the present invention will be described in detail with reference to the accompanying drawings. However, the present invention is not limited to a specific disclosure type, but should be construed as including all modifications, equivalents, substitutes involved in the scope and the technological range of the present invention.

Examples 1-6

Preparation of Lipid Compositions Forming Liquid Crystal

Phospholipid, sorbitan unsaturated fatty acid ester, a liquid crystal hardener, and ethanol were added in the amount as shown in Table 1 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (PowerGenmode1123, Fisher) at a rate of 1,000-3,000 RPM for 5-10 minutes, and a composition for liquid crystals in a solution phase was obtained. Table 1 below shows the weight ratios for the final components of the compositions prepared thereof.

TABLE 1

| Unit (mg) | Ex. 1 | Ex. 2 | Ex. 3 | Ex. 4 | Ex. 5 | Ex. 6 |
|---|---|---|---|---|---|---|
| Lipoid S-100[1] | 1.39 | 6.95 | 13.90 | 1.39 | 6.95 | 13.90 |
| Sorbitan monooleate | 0.92 | 2.30 | 4.60 | — | — | — |
| Sorbitan sesquinoleate | — | — | — | 0.92 | 2.30 | 4.60 |
| Polysorbate 80 | 0.05 | — | 0.50 | — | 0.25 | 0.50 |
| Tocopherol acetate | 0.18 | 0.45 | 0.90 | 0.18 | 0.45 | 0.90 |
| Ethanol | 0.36 | 0.45 | 0.60 | 0.90 | 0.36 | 0.45 |
| Poloxamer 407 | 1.1 | 1.1 | 1.1 | 1.1 | 1.1 | 1.1 |

[1]Lipoid S-100 consists of phosphotidylcholine, phospatidylethanolamine, phosphatidylinositol, and lysophosphatidylcholine, and includes phosphatidylcholine more than 94% as a major component.

Examples 7-13

Preparation of Composites with Gene, Chitosan, Protamine, Sodium Lauryl Sulfate, and Liquid Crystal Forming Lipid Composition Phospholipid, sorbitan unsaturated fatty acid ester, a liquid crystal hardener, and ethanol were added in the amount as shown in Table 2 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (Power Gen Model 123, Fisher) at a rate of 1,000-3,000 RPM for 5-10 minutes, and obtained was a composition for liquid crystals in a solution phase.

When gene delivery is to be performed by further adding sodium lauryl sulfate, survivin siRNA, which is to be delivered as an active material, was mixed with sodium lauryl sulfate in a weight ratio of 1:1 (w/w), and the mixture was prepared at the concentration of 20 mg/mL using water for injection. Chitosan HCl having a molecular weight of 150 kDa, protamine and poloxamer 407 were mixed at weight ratios shown in Table 2 below and prepared at a concentration of 8 mg/mL using water for injection, and then mixed with 20 mg/mL of the mixed solution including survivin siRNA and sodium lauryl sulfate, at a volume ratio of 1:2.5 (v/v) and agitated thereafter. The survivin siRNA mixed solution which does not include sodium lauryl sulfate was prepared in the same manner as above except for the step of mixing sodium lauryl sulfate.

Finally, the thus prepared liquid crystal composition was added with survivin siRNA mixed solution according to the weight ratios shown in Table 2 below to obtain composites and the resulting composites were filtered using a 0.22 μm filter. The survivin siRNA used had a sense sequence of 5'-AAG GAG AUC AAC AUU UUC A(dTdT)-3', and an antisense sequence of 5'-UGA AAA UGU UGA UCU CCU U(dTdT)-3'. Table 2 below shows the weight ratios of final components of the thus prepared compositions.

TABLE 2

| Unit (ug) | Ex. 7 | Ex. 8 | Ex. 9 | Ex. 10 | Ex. 11 | Ex. 12 | Ex. 13 |
|---|---|---|---|---|---|---|---|
| Lipoid S-100[1] | 1.39 | 1.39 | 1.39 | 1.39 | 1.39 | 1.39 | 1.39 |
| Sorbitan monooleate | 0.92 | 0.92 | 0.92 | 0.92 | 0.92 | 0.92 | 0.92 |
| Polysorbate 80 | 0.05 | 0.05 | 0.05 | 0.05 | 0.05 | 0.05 | 0.05 |
| Tocopherol acetate | 0.18 | 0.18 | 0.18 | 0.18 | 0.18 | 0.18 | 0.18 |
| Ethanol | 0.36 | 0.36 | 0.36 | 0.36 | 0.36 | 0.36 | 0.36 |
| Poloxamer 407 | 2.20 | 2.20 | 2.20 | 2.20 | 2.20 | 2.20 | 2.20 |
| Survivin siRNA | 1.00 | 1.00 | 1.00 | 1.00 | 1.00 | 1.00 | 1.00 |
| Sodium lauryl sulfate | — | 1.00 | — | 1.00 | 1.00 | 1.00 | 1.00 |
| Protamine | — | — | 0.60 | 0.60 | 0.60 | 0.60 | 0.60 |
| Chitosan HCl | 0.30 | 0.30 | 0.30 | 0.30 | 5.00 | 10.00 | 20.00 |

Examples 14-19

Preparation of Composites with Gene, Chitosan, Protamine, Thiamine Pyrophosphate and Liquid Crystal Forming Lipid Composition Phospholipid, sorbitan unsaturated fatty acid ester, a liquid crystal hardener, and ethanol were added in the amount as shown in Table 3 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (PowerGenmodel123, Fisher) at a rate of 1,000-3,000 RPM, and a composition for liquid crystals in a solution phase was obtained.

20 mg of survivin siRNA, the gene to be delivered as an active material, 30 mg of chitosan HCl having a molecular weight of 150 kDa, 30 mg of thiamine pyrophosphate and 1 mg of protamine were dissolved in 1 mL of water for injection, respectively. The survivin siRNA mixed solution which does not include thiamine pyrophosphate was prepared in the same manner except for the step of dissolving thiamine pyrophosphate in 1 mL of water for injection.

The thus prepared liquid crystal composition and each of the aqueous solutions prepared thereof were added according to the weight ratios shown in Table 3 to obtain a composite and the resulting composite was filtered using a 0.22 μm filter. Table 3 below shows the weight ratios of final components of the thus prepared compositions.

TABLE 3

| Unit (ug) | Ex. 14 | Ex. 15 | Ex. 16 | Ex. 17 | Ex. 18 | Ex. 19 |
|---|---|---|---|---|---|---|
| Lipoid S-100[1] | 1.39 | 1.39 | 1.39 | 1.39 | 0.35 | 0.35 |
| Sorbitan monooleate | 0.92 | 0.92 | 0.92 | 0.92 | 0.23 | 0.23 |
| Polysorbate 80 | 0.05 | 0.05 | 0.05 | 0.05 | 0.01 | 0.01 |
| Tocopherol acetate | 0.18 | 0.18 | 0.18 | 0.18 | 0.05 | 0.05 |
| Ethanol | 0.36 | 0.36 | 0.36 | 0.36 | 0.09 | 0.09 |
| Poloxamer 407 | 0.28 | 0.28 | 0.28 | 0.28 | 0.28 | 0.50 |
| Survivin siRNA | 1.00 | 1.00 | 1.00 | 1.00 | 1.00 | 1.00 |
| Thiamine pyrophosphate | — | — | 1.00 | 1.00 | 4.00 | 6.00 |
| Protamine | — | 0.60 | — | 0.60 | 0.60 | 0.60 |
| Chitosan HCl | 0.30 | 0.30 | 0.30 | 0.30 | 0.30 | 0.30 |

Examples 20-24

Preparation of Lyophilizate of Composites with Liquid Crystal Forming Lipid Composition, Gene, Chitosan, Protamine and Sodium Lauryl Sulfate Phospholipid, sorbitan unsaturated fatty acid ester, a liquid crystal hardener, and ethanol were added in the amount as shown in Table 4 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (PowerGenmodel123, Fisher) at a rate of 1,000-3,000 RPM, and a composition for liquid crystals in a solution phase was obtained.

Survivin siRNA and sodium lauryl sulfate were mixed in a weight ratio of 1:1 (w/w), and the mixture was prepared at a concentration of 20 mg/mL using water for injection. Chitosan HCl with a molecular weight of 150 kDa, protamine and poloxamer 407 was mixed at a weight ratio of 1:2:4 (w/w) and prepared at a concentration of 8 mg/mL using water for injection, and then mixed with 20 mg/mL of the mixed solution including survivin siRNA and sodium lauryl sulfate, at a volume ratio of 1:2.5 (v/v) and agitated thereafter. The survivin siRNA mixed solution which does not include sodium lauryl sulfate was prepared in the same manner as above except for the step of mixing sodium lauryl sulfate.

The thus prepared liquid crystal composition was added with the survivin siRNA mixed solution according to the weight ratios shown in Table 4 to obtain a composite and the resulting composite was filtered using a 0.22 μm filter. In order to lyophilize the thus prepared composite, an excipient prepared by using 30% solution in advance was mixed according to the weight ratios shown in Table 4, frozen at −70° C., and lyophilized to obtain a solid phase product.

TABLE 4

| Unit (ug) | Ex. 20 | Ex. 21 | Ex. 22 | Ex. 23 | Ex. 24 |
| --- | --- | --- | --- | --- | --- |
| Lipoid S-100[1)] | 1.39 | 1.39 | 1.39 | 1.39 | 1.39 |
| Sorbitan monooleate | 0.92 | 0.92 | 0.92 | 0.92 | 0.92 |
| Polysorbate 80 | 0.05 | 0.05 | 0.05 | 0.05 | 0.05 |
| Tocopherol acetate | 0.18 | 0.18 | 0.18 | 0.18 | 0.18 |
| Ethanol | 0.36 | 0.36 | 0.36 | 0.36 | 0.36 |
| Poloxamer 407 | 2.20 | 2.20 | 2.20 | 2.20 | 2.20 |
| Survivin siRNA | 1.00 | 1.00 | 1.00 | 1.00 | 1.00 |
| Sodium lauryl sulfate | — | — | 1.00 | 1.00 | 1.00 |
| Protamine | — | 0.60 | — | 0.60 | 0.60 |
| Chitosan | 0.30 | 0.30 | 0.30 | 0.30 | 0.30 |
| Trehalose | 23.00 | 23.00 | 23.00 | 23.00 | |
| Glucose | | | | | 23.00 |

Comparative Example 1

Preparation of Composite with Liquid Crystal Forming Lipid Composition, Gene, Protamine, and Sodium Lauryl Sulfate In order to compare the producing capability of a composite for gene delivery according to its presence/absence of chitosan, composites for gene delivery without chitosan were manufactured and compared. In particular, phospholipid, sorbitan unsaturated fatty acid ester, a liquid crystal hardener, and ethanol were added in the amount as shown in Table 5 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (PowerGenmode1123, Fisher) at a rate of 1,000-3,000 RPM, and a composition for liquid crystals in a solution phase was obtained.

Survivin siRNA and sodium lauryl sulfate were mixed at a weight ratio of 1:1 (w/w), and the mixture was prepared at a concentration of 20 mg/mL using water for injection. Protamine and poloxamer 407 were mixed at a weight ratio of 2:4 (w/w) and prepared at a concentration of 8 mg/mL using water for injection, and then mixed with 20 mg/mL of the mixed solution including survivin siRNA and sodium lauryl sulfate, at a volume ratio of 1:2.5 (v/v) and agitated thereafter. The survivin siRNA mixed solution which does not include sodium lauryl sulfate was prepared in the same manner as above except for the step of mixing sodium lauryl sulfate.

The thus prepared lipid solution was added with the survivin siRNA mixed solution according to the weight ratios shown in Table 5 to obtain a composite and the resulting composite was filtered using a 0.22 μm filter.

TABLE 5

| Unit (ug) | Comp. Ex. 1 |
| --- | --- |
| Lipoid S-100[1)] | 1.39 |
| Sorbitan monooleate | 0.92 |
| Polysorbate 80 | 0.05 |
| Tocopherol acetate | 0.18 |
| Ethanol | 0.36 |
| Poloxamer 407 | 2.20 |
| Survivin siRNA | 1.00 |
| Sodium lauryl sulfate | 1.00 |
| Protamine | 0.60 |

Comparative Examples 2 and 3

Preparation of Composite with Genetic Drug Consisting of Gene, Chitosan, Thiamine Pyrophosphate and Protamine In order to confirm whether a composite for gene delivery can be formed in the absence of a material which forms liquid crystals, composites not including a material which forms liquid crystals were manufactured.

First, 30 mg of chitosan HCl having a molecular weight of 150 kDa, 2 mg of thiamine pyrophosphate, and 0.5 mg of protamine were dissolved in 1 mL of water for injection, respectively, and the thus prepared aqueous solutions were mixed according to the weight ratios shown in Table 6 to obtain a composite.

TABLE 6

| Unit (ug) | Comp. Ex. 2 | Comp. Ex. 3 |
| --- | --- | --- |
| Survivin siRNA | 1.00 | 1.00 |
| Thiamine pyrophosphate | 17.10 | 17.10 |
| Protamine | | 0.60 |
| Chitosan HCl | 2.90 | 2.90 |

Comparative Example 4

Preparation of Composites Between a Gene, Water-Soluble Chitosan, Protamine, Sodium Lauryl Sulfate and a Liquid Crystal Forming Lipid Composition In order to confirm whether a gene included as an active material is effectively delivered for the intended purpose, a comparative group including fluorescein-labeled dsRNA oligomer (FL dsRNA, Invitrogen), which is a gene not capable of inhibiting tumor growth, was prepared instead of the survivin siRNA, and used as a control group to compare the effectiveness of gene delivery.

First, phospholipid, sorbitan unsaturated fatty acid ester, a liquid crystal hardener, and ethanol were added in the amount as shown in Table 7 below, and the mixture was agitated at room temperature to obtain a uniform lipid solution.

0.15 mL of the lipid solution was added into 5 mL of 1.1% poloxamer 407 aqueous solution, and homogenized at 20-75° C. using an ultrasonicator or a homogenizer (PowerGenmode1123, Fisher) at a rate of 1,000-3,000 RPM, and a composition for liquid crystals in a solution phase was obtained.

FL dsRNA and sodium lauryl sulfate were mixed at a weight ratio of 1:1 (w/w), and the mixture was prepared at a concentration of 20 mg/mL using water for injection. The nucleotide sequence used for FL dsRNA was 5'-UUG UUU UGG AGC ACG GAA A(dTdT)-3'. Chitosan HCl having a molecular weight of 150 kDa, protamine and poloxamer 407 were mixed at a weight ratio of 1:2:4 (w/w) and prepared at a concentration of 8 mg/mL using water for injection, and then mixed with 20 mg/ml of the mixed solution including survivin siRNA and sodium lauryl sulfate, at a volume ratio of 1:2.5 (v/v) and agitated thereafter.

The thus prepared lipid solution was added with the FL dsRNA mixed solution according to the weight ratio shown in Table 7 to obtain a composite and the resulting composite was filtered using a 0.22 μm filter.

TABLE 7

| Unit (ug) | Comp. Ex. 4 |
| --- | --- |
| Lipoid S-100 | 1.39 |
| Sorbitan monooleate | 0.92 |
| Polysorbate 80 | 0.05 |
| Tocopherol acetate | 0.18 |
| Ethanol | 0.36 |
| Poloxamer 407 | 2.20 |
| FL dsRNA | 1.00 |
| Sodium lauryl sulfate | 1.00 |
| Protamine | 0.60 |
| Chitosan HCl | 0.30 |

Experimental Example 1

Confirmation of Structures of Liquid Crystals in an Aqueous Fluid Phase

In order to confirm the structures of liquid crystals formed in an aqueous fluid phase by the lipid compositions prepared in Examples 1-6 using a polarization microscope (Motic, BA 300 Pol), the lipid compositions prepared in Examples 1-6 were very thinly applied on slide glasses, placed in Chalet including triple distilled water for 4 hours to form liquid crystals on slide glasses.

The slide glasses were covered with cover glasses to prevent introduction of any air thereinto, and were observed under a polarization microscope (Motic, BA 300 Pol) at 200× magnification.

Figure 1A:
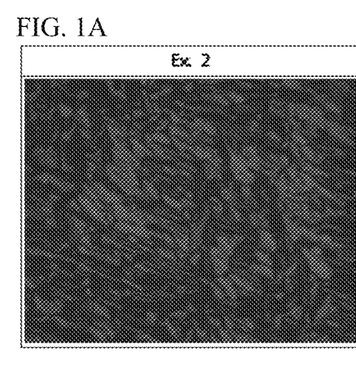
FIG. 1A shows a picture of the structures of liquid crystals in an aqueous fluid prepared in Example 2.
Figure 1B:
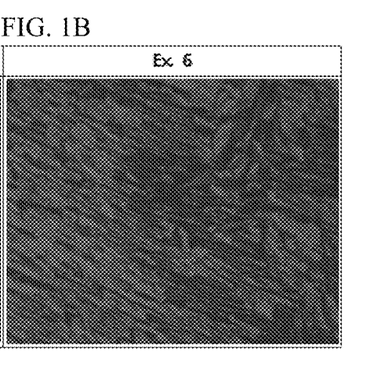
FIG. 1B shows a picture of the structures of liquid crystals in an aqueous fluid prepared in Example 6.

The results are shown in FIG. 1A and FIG. 1B.

As shown in FIGS. 1A and 1B, the structures of liquid crystals of the lipid compositions prepared in Examples 2 and 6, respectively, were confirmed to have the typical hexagonal structure which can provide excellent particle stability.

Experimental Example 2

Observation of Composites with Gene, Chitosan, Sodium Lauryl Sulfate, Protamine and Liquid Crystal Forming Lipid Composition Under Cryo Transmission Electron Microscope The lipid compositions prepared in Examples 2, 6 and 10 were observed under Cryo transmission electron microscopy (Cryo-TEM) (Tecnai 12 electron microscope, Philips, the Netherlands), and the formation of liquid crystal composite compositions for gene delivery was confirmed. The compositions were placed on top of grids in the form of thin meninges, and lyophilized at −170° C. The composites of the lyophilized compositions on top of the grids were observed according to the user's manual by the manufacturer.

Figure 2A:
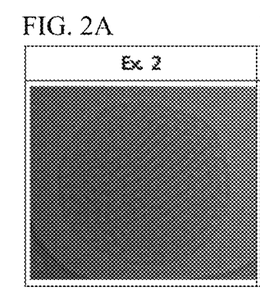
FIGS. 2A-2C show pictures of the structures of liquid crystals in an aqueous fluid prepared in Examples 2 (FIG. 2A), 6 (FIG. 2B), and 10 (FIG. 2C), respectively, via Cryo transmission electron microscopy (Cryo-TEM).
Figure 2B:
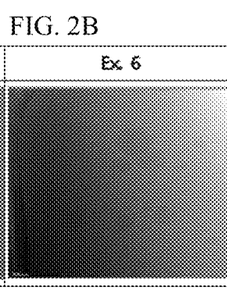
Figure 2C:
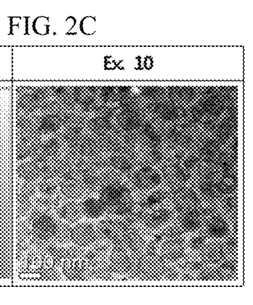

The results are shown in FIGS. 2A-2C.

As shown in FIGS. 2A and 2B, it was confirmed that the lipid compositions prepared in Examples 2 and 6, respectively, formed the typical liquid crystals because they formed a spherically hexagonal type of a net in an aqueous fluid phase. Additionally, in Example 10, as shown in FIG. 2C, it was confirmed that the liquid crystal composite composition for gene delivery consisting of a gene, water-soluble chitosan, sodium lauryl sulfate, protamine, and a liquid crystal forming lipid composition formed a typical spherical type of a nanocomposite.

Experimental Example 3

Measurement of Particle Size Using Composites with a Gene, Chitosan, Sodium Lauryl Sulfate, Thiamine Pyrophosphate, Protamine, and a Liquid Crystal Forming Lipid Composition The particle size of the compositions prepared in Examples 7, 10, 12, 13, 14, 17, and 19, and Comparative Example 1 was measured using Electrophoretic Light Scattering Spectrophotometer (ELS) particle size and electric charge analyzer (ELS-Z, Otsuka, Japan). The particle size of the compositions was measured using particle size cell according to the user's manual by the manufacturer. The results are shown in FIG. 3.

Figure 3:
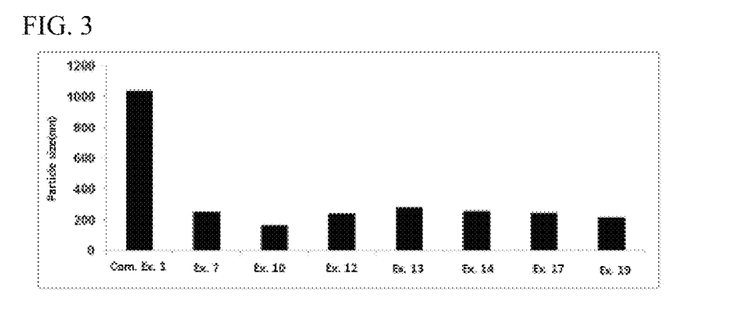
FIG. 3 is a graph showing the particle size of liquid crystals in Examples 7, 10, 12, 13, 14, 17, 19 and Comparative Example 1.

As shown in FIG. 3, it was confirmed that all the liquid crystal composite compositions for gene delivery which selectively do not include protamine in the composite compositions, which include a gene, water-soluble chitosan and a liquid crystal forming lipid composition (Examples 7 and 14), or those which further include sodium lauryl sulfate (Examples 10, 12, and 13) or thiamine pyrophosphate (Examples 17 and 19) were all shown to have a uniform particle size in the range of 200-300 nm. However, the composite compositions, which not include chitosan (Comparative Example 1) was shown to has ununiform particle size and the particle size became bigger. Accordingly, it was confirmed that chitosan is essential in forming a composite having a uniform particle diameter suitable for cell penetration.

Experimental Example 4

Observation of the Inhibitory Effect Against Target Protein Expression by Composites with a Gene, Chitosan, Sodium Lauryl Sulfate, Thiamine Pyrophosphate, Protamine, and a Liquid Crystal Forming Lipid Composition In order to evaluate the inhibitory effect against target protein expression by the groups treated with compositions prepared in Comparative Example 1, Examples 7, 10, 12, 13, 14, 17, and 19, and by groups treated with a gene alone, experiments were performed by a method described below using a survivin ELISA kit (R&D systems, catalog No. SVE00). A human prostate cancer cell line (PC-3, ATCC) was aliquoted into a 6-well plate so that each well has 1×105 cells, and incubated in a 10% fetal bovine serum(FBS)-containing medium (pH 7.2) at 37° C., 5% $CO_2$ condition for 48 hours. Prior to administration of a genetic drug, the medium was replaced with a fresh 10% FBS-containing medium (pH7.2), and then stabilized for 2 hours. Then, compositions prepared in Comparative Example 1, Example 7, 10, 12, 13, 14, 17, and 19, and a gene alone were respectively added to the prostate cancer cell line and incubated at 37° C., 5% $CO_2$ condition for 48 hours. The genetic drug administered was 2 μg/well. Upon completion of the incubation, the medium was removed and added with 500 μl of cell lysis buffer (cell signaling technology) to collect the prostate cancer cell line. Additionally, the collected material was centrifuged at 12,000 rpm for 20 minutes in order to separate cell residues from the supernatant. The inhibitory effect against target protein expression was compared by using 100 μl of the supernatant, and the amount of protein expression of survivin contained in the medium sample was measured using survivin ELISA kit according to the user's manual of the manufacturer.

Figure 4:
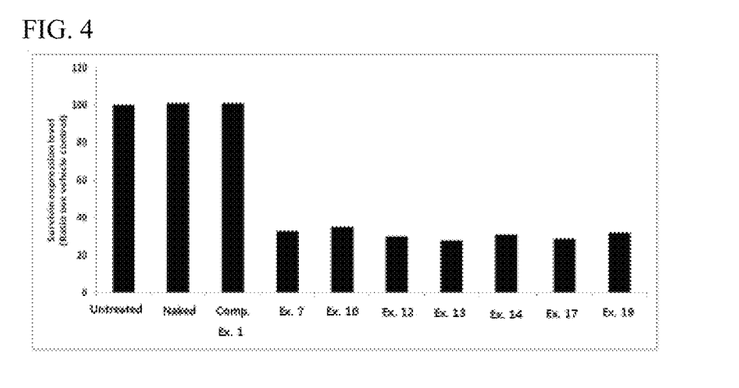
FIG. 4 is a graph showing the observation results of the inhibitory capability of the liquid crystals prepared in Examples 7, 10, 12, 13, 14, 17, 19 and Comparative Example 1 against target proteins.

The results are shown in FIG. 4.

As shown in FIG. 4, it was confirmed that the liquid crystal composite compositions for gene delivery which selectively do not include protamine in the composite compositions, which include a gene, water-soluble chitosan and a liquid crystal forming lipid composition (Examples 7 and 14), or those which further include sodium lauryl sulfate (Examples 10, 12, and 13) or thiamine pyrophosphate (Examples 17 and 19) were all shown to effectively inhibit the expression of target proteins via effective gene delivery into cells. In contrast, in a composite treated with a gene alone or in a composite where chitosan is absent (Comparative Example 1), the expression of target proteins was not inhibited at all. From the above, it was confirmed that cationic chitosan is essential for effective gene delivery although cationic protamine is present. That is, chitosan plays a crucial role in the composite according to the present invention, and the gene delivery function is completely lost in the absence of chitosan.

Experimental Example 5

Safety Evaluation in Blood Serum of Composites with a Gene, Chitosan, Sodium Lauryl Sulfate, Thiamine Pyrophosphate, Protamine, and a Liquid Crystal Forming Lipid Composition In order for chitosan to have in vivo biocompatibity as a gene delivery vector it is essential to secure its particle stability in blood serum but chitosan has the drawback that it causes precipitation in blood serum and is thus incapable of gene delivery. Accordingly, in order to confirm whether the liquid crystal composite compositions for gene delivery of the present invention can form stable particles in blood serum, the composites prepared in Examples of the present invention were compared with those in Comparative Examples 2 and 3, which do not include a liquid crystal formation material.

More specifically, composites prepared in Comparative Examples 2 and 3 and Examples 10, 17, 18 and 19 were mixed so that blood serum can be 50%, and in 3 hours, the change in particle size was measured using Electrophoretic Light Scattering Spectrophotometer (ELS) particle size and electric charge analyzer (ELS-Z, Otsuka, Japan). The particle size of the compositions was respectively measured using particle size cell according to the user's manual by the ELS manufacturer.

Figure 5:
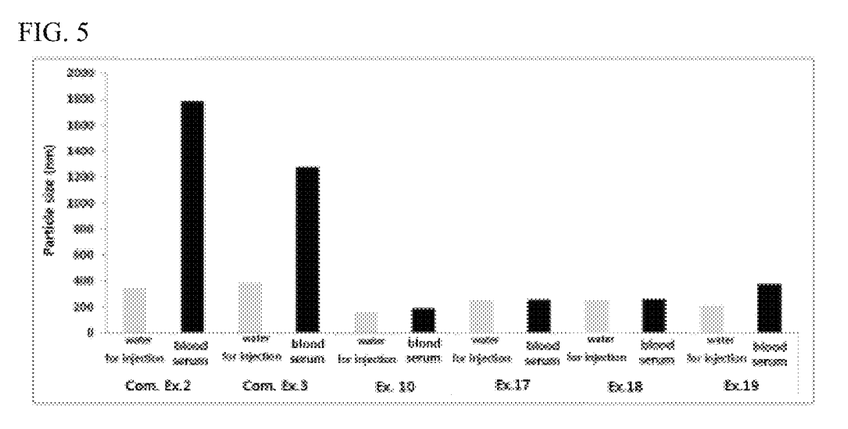
FIG. 5 is a graph showing the stability of particles in blood serum of the liquid crystals prepared in Examples 10, 17 18, 19, and Comparative Examples 2 and 3.

The results are shown in FIG. 5.

As shown in FIG. 5, it was confirmed that the liquid crystal composite compositions for gene delivery which selectively further include sodium lauryl sulfate (Example 10) or thiamine pyrophosphate (Examples 17, 18, and 19) in the composite composition including a gene, water-soluble chitosan and a liquid crystal forming lipid composition maintained their particle size at the initial manufactured state to be in the range of 200-300 nm even in the blood serum. In contrast, in composites for gene delivery prepared excluding the lipid composition for forming liquid crystals (Comparative Examples 2 and 3), particles were 1,500 nm, 1,200 nm, respectively, were not capable of maintaining particle stability due to the severe agglutination with proteins present in the blood serum. Accordingly, it was confirmed that the present invention, by constituting a liquid crystal forming lipid composition along with chitosan, secures particle stability in the blood serum, and effectively performs delivery of a target gene while resolving the problems in the existing technology.

Experimental Example 6

Manufacture of Lyophilized Products Using Composites with a Gene, Chitosan, Sodium Lauryl Sulfate, Protamine, and a Liquid Crystal Forming Lipid Composition, and Measurement of Particle Size of the Same In order to confirm whether the liquid crystal composite composition of the present invention can be lyophilized for the purpose of easiness of storage and distribution, the compositions were lyophilized and then redispersed to confirm the particle size.

More specifically, the compositions prepared in Examples 23 and 24 in which trehalose and glucose as saccharides were additionally included were lyophilized and then redispersed with purified water to prepare the gene at a concentration of 100 μg/mL, and the particle size was observed using an Electrophoretic Light Scattering Spectrophotometer (ELS) particle size and electric charge analyzer (ELS-Z, Otsuka, Japan). The particle size of the compositions was respectively measured using particle size cell according to the user's manual by the ELS manufacturer.

Figure 6:
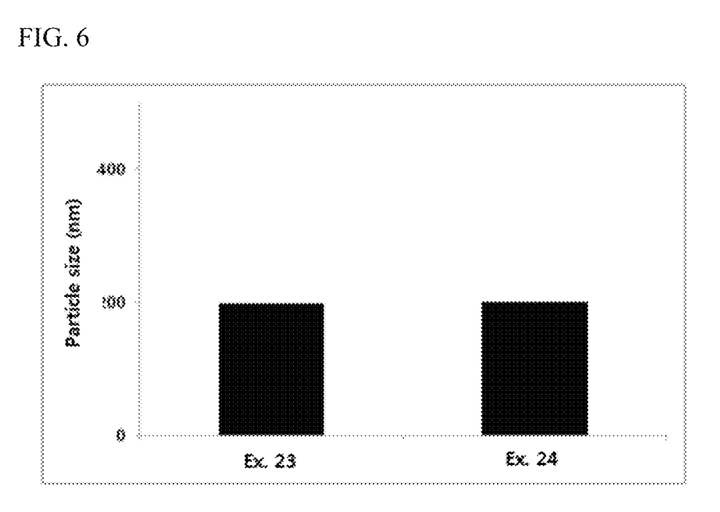
FIG. 6 is a graph showing the size of particles of the liquid crystals prepared in Examples 23 and 24 after lyophilization.

The results are shown in FIG. 6.

As shown in FIG. 6, it was confirmed that the compositions prepared in Examples 23 and 24 were able to maintain the initial particle size at about 200 nm even when they were rehydrated after lyophilization. Based on the above, particle stability at the level of before lyophilization can be maintained even when the compositions are lyophilized by further adding a saccharide and applied in vivo, thus confirming that the liquid crystal composite composition for gene delivery can be stably stored in the form of a lyophilized product during storage and distribution.

Experimental Example 7

Evaluation of In Vivo Tumor Growth Inhibitory Effect by Composites with a Gene, Chitosan, Sodium Lauryl Sulfate, Protamine, and a Liquid Crystal Forming Lipid Composition In order to confirm whether the gene being delivered by the liquid crystal composition for gene delivery of the present invention can be delivered inside a living body and effectively exhibit the intended purpose, the tumor inhibitory effect by the composition prepared in Example 10 which includes survivin siRNA as a gene, and the composition prepared in Comparative Example 4 which includes FL dsRNA, which is incapable of tumor inhibitory effect, as a gene. In order to evaluate the in vivo delivery capability of a genetic drug, an immunodeficient mouse model transplanted with a prostate cancer was used. In order to construct an immunodeficient mouse model transplanted with a prostate cancer, $2\times10^6$ cells of prostate cancer cell line redispersed in 50 µl of RPMI culture medium was mixed with 50 µl of Matrigel (BD biosciences), and the mixture was subcutaneously injected into 5 week old immunodeficient mice. The size of tumor was grown to the size of 100 mm$^3$, and then the compositions prepared in Example 10 and Comparative Example 4 to include the amount of gene at 200 µg/mL were respectively injected into the tail vein of mice. The amount of a single dose of the genetic drug was 40 µg and administered 6 times over a period of 2 weeks.

Figure 7:
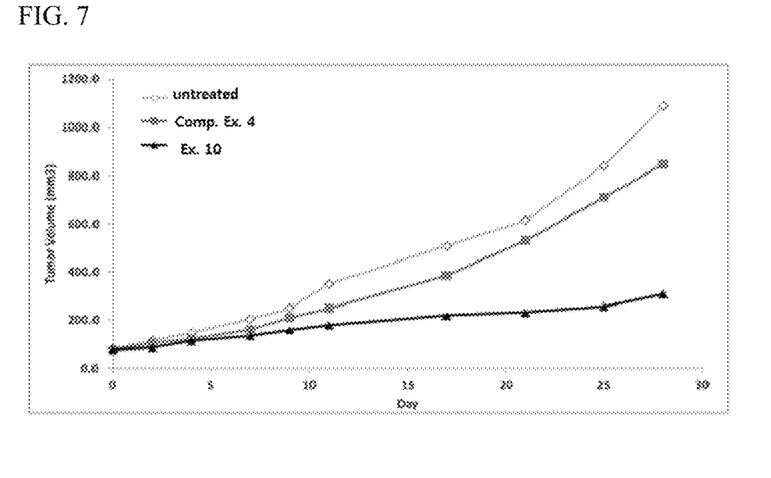
FIG. 7 is a graph showing the observation results of the inhibitory capability of the liquid crystals prepared in Example 10 and Comparative Example 4 against tumor growth.

The results are shown in FIG. 7.

As shown in FIG. 7, when a composite composition for gene delivery consisting of a gene, water-soluble chitosan, sodium lauryl sulfate, protamine, and a liquid crystal forming lipid composition (Example 10) was intravenously injected into the immunodeficient mouse model transplanted with a prostate cancer, it was observed that in vivo tumor proliferation was considerably inhibited. In the group of mice intravenously injected with the composition prepared in Example 10 of the present invention, the tumor inhibitory rate was about 63% on the last day of the injection (Day 11) and about 70% on a week thereafter (Day 18), respectively, as compared with that of the untreated group. In contrast, in the mice belonging to the untreated group and in the group treated with a composite composition including a gene not capable of tumor suppression (Comparative Example 4), the tumor was shown to continue to grow without any noticeable inhibition. From the above, it was confirmed that the composite composition for gene delivery of the present invention can be effectively delivered via an in vivo intravenous injection, and also the gene delivered can effectively perform the intended effect.

Conclusively, the compositions of the present invention were confirmed that they can exhibit a superior gene delivery effect via systemic administration, and also they resolved the bioincompatibility of the conventional chitosan as a gene delivery drug due to its relatively low binding strength with a gene and instability in blood serum.

INDUSTRIAL APPLICABILITY

The compositions of the present invention including chitosan and a liquid crystal formation material for gene delivery have overcomed the low binding strength of chitosan with a gene, and also considerably improved the stability of chitosan nanocomposite in blood serum, enabling high efficiency gene delivery and superior stability, thus being useful as a gene therapeutic agent.

The invention claimed is:

1. An aqueous injectable composition, comprising:
   (a) a liquid crystal formation material consisting of a sorbitan unsaturated fatty acid ester that has at least two hydroxyl groups in the polar head group;
   (b) a phospholipid;
   (c) a liquid crystal hardener;
   (d) chitosan or its salts;
   (e) a dispersing agent that is one or more selected from among a poloxamer, polyvinylalcohol, polyethylene glycol-glyceryl monooleate, hydrophobically modified starch, and a combination thereof;
   (f) a nucleic acid molecule comprising a gene or encoding a gene product for gene therapy;
   (g) protamine or pharmaceutically acceptable salts thereof,
   (h) sodium lauryl sulfate; and
   (i) water,
   wherein:
   the aqueous injectable composition is formulated to be administered via an intravenous injection, an intramuscular injection, a subcutaneous injection, an intrauterine injection, or a cerebrovascular injection for effecting gene therapy;
   the sorbitan unsaturated fatty acid ester is one or more selected from among sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate, and a combination thereof;
   the phospholipid is at least one selected from among phosphatidylcholine, phosphatidylethanolamine, phosphatidylserine, phosphatidylglycerine, phosphatidylinositol, phosphatidic acid, sphingomyelin, and a combination thereof;
   the liquid crystal hardener is at least one selected from among tocopherol acetate, cholesterol, benzyl benzoate, ubiquinone, and a combination thereof;
   the salt of chitosan is at least one selected from among chitosan HCl, chitosan acetate, chitosan glutamate, and chitosan lactate;
   the nucleic acid molecule is at least one selected from among single-stranded DNA, double-stranded DNA, single-stranded RNA, double-stranded RNA, plasmid DNA, single-stranded siRNA, double-stranded siRNA, an anti sense oligonucleotide, a ribozyme, a catalytic RNA, and a polymer of nucleotides;
   the sorbitan unsaturated fatty acid ester, the phospholipid, and the liquid crystal hardener are included in a weight ratio of 0.20-1:1-1.5:0.05-0.2;
   components (a)-(c) form a liquid crystal having a non-lamellar structure in an aqueous fluid;
   the liquid crystal consists of the liquid crystal formation material, the phospholipid and the liquid crystal hardener;
   the aqueous injectable composition comprises a nanocomposite having a size from about 10 to 500 nm; and
   the nanocomposite comprises the liquid crystal, the chitosan or its salts and the nucleic acid molecule.

2. The composition of claim 1, further comprising thiamine pyrophosphate or pharmaceutically acceptable salts thereof.

3. The composition of claim 1, further comprising at least one saccharide selected from among mannose, fructose, arabinose, trehalose, maltose, cellobiose, isomaltose, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin, and sulfobutylether β-cyclodextrin.

4. The composition of claim 1, further comprising a stabilizing agent, a buffer, a preservative, an analgesic agent, and a tonicity agent.

5. The composition of claim 1, wherein the chitosan is in the form of a coating.

6. A composition for gene delivery, comprising:
a first solution capable of forming a liquid crystal having a non-lamellar structure in an aqueous fluid, comprising a liquid crystal formation material consisting of a sorbitan unsaturated fatty acid ester which has at least two hydroxyl groups in the polar head group, a phospholipid, and a liquid crystal hardener,
wherein:
the sorbitan unsaturated fatty acid ester is one or more selected from among sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate, and a combination thereof;
the phospholipid is at least one selected from among phosphatidylcholine, phosphatidylethanolamine, phosphatidylserine, phosphatidylglycerine, phosphatidylinositol, phosphatidic acid, sphingomyelin, and a combination thereof;
the liquid crystal hardener is at least one selected from among tocopherol acetate, cholesterol, benzyl benzoate, ubiquinone, and a combination thereof; and
the sorbitan unsaturated fatty acid ester, phospholipid, and the liquid crystal hardener are included in a weight ratio of 0.20-1:1-1.5:0.05-0.2; and
a second solution comprising:
chitosan or its salts;
a dispersing agent selected from among one or more of a poloxamer, polyvinylalcohol, polyethylene glycolglyceryl monooleate, hydrophobically modified starch, and a combination thereof;
a nucleic acid molecule comprising a gene or encoding a gene product for gene therapy;
protamine or pharmaceutically acceptable salts thereof;
sodium lauryl sulfate; and
water,
wherein:
the salt of chitosan is at least one selected from among chitosan HCl, chitosan acetate, chitosan glutamate, and chitosan lactate;
the nucleic acid molecule is at least one selected from among single-stranded DNA, double-stranded DNA, single-stranded RNA, double-stranded RNA, plasmid DNA, single-stranded siRNA, double-stranded siRNA, an antisense oligonucleotide, a ribozyme, a catalytic RNA, and a polymer of nucleotides;
a nanocomposite is formed upon mixing the two solutions;
the nanocomposite comprises a liquid crystal, the chitosan or its salts and the nucleic acid molecule;
the liquid crystal consists of the liquid crystal formation material, the phospholipid and the liquid crystal hardener; and
the composition is formulated to be administered via an intravenous injection, an intramuscular injection, a subcutaneous injection, an intrauterine injection, or a cerebrovascular injection for effecting gene therapy.

7. A lyophilized preparation of a composition for gene delivery, wherein the composition comprises:
(a) a liquid crystal formation material consisting of a sorbitan unsaturated fatty acid ester which has at least two hydroxyl groups in the polar head group;
(b) a phospholipid;
(c) a liquid crystal hardener;
(d) chitosan or its salts;
(e) a dispersing agent, selected from among one or more of a poloxamer, polyvinylalcohol, polyethylene glycolglyceryl monooleate, hydrophobically modified starch, and a combination thereof;
(f) a nucleic acid molecule comprising a gene or encoding a gene product for gene therapy;
(g) protamine or pharmaceutically acceptable salts thereof, and
(h) sodium lauryl sulfate,
wherein:
the composition is formulated to be administered via an intravenous injection, an intramuscular injection, a subcutaneous injection, an intrauterine injection, or a cerebrovascular injection for effecting gene therapy;
the sorbitan unsaturated fatty acid ester is one or more selected from among sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate, and a combination thereof;
the phospholipid is at least one selected from among phosphatidylcholine, phosphatidylethanolamine, phosphatidylserine, phosphatidylglycerine, phosphatidylinositol, phosphatidic acid, sphingomyelin, and a combination thereof;
the liquid crystal hardener is at least one selected from among tocopherol acetate, cholesterol, benzyl benzoate, ubiquinone, and a combination thereof;
the sorbitan unsaturated fatty acid ester, phospholipid, and the liquid crystal hardener are included in a weight ratio of 0.20-1:1-1.5:0.05-0.2;
the salt of chitosan is at least one selected from among chitosan HCl, chitosan acetate, chitosan glutamate, and chitosan lactate;
the nucleic acid molecule is at least one selected from among single-stranded DNA, double-stranded DNA, single-stranded RNA, double-stranded RNA, plasmid DNA, single-stranded siRNA, double-stranded siRNA, an anti sense oligonucleotide, a ribozyme, a catalytic RNA, and a polymer of nucleotides;
components (a)-(c) form a liquid crystal having a non-lamellar structure in an aqueous fluid;
the liquid crystal consists of the liquid crystal formation material, the phospholipid, and the liquid crystal hardener; and
the preparation is a solid lyophilized preparation.

8. The lyophilized preparation of claim 7, further comprising an excipient for lyophilization.

9. The lyophilized preparation of claim 8, wherein the excipient for lyophilization is a sugar alcohol or a saccharide.

10. The lyophilized preparation of claim 9, wherein the saccharide is at least one selected from among mannose, fructose, arabinose, trehalose, maltose, cellobiose, isomaltose, dextrin, α-cyclodextrin, β-cyclodextrin, γ-cyclodextrin, hydroxypropyl-β-cyclodextrin, hydroxyethyl-β-cyclodextrin, dimethyl-β-cyclodextrin, trimethyl-β-cyclodextrin, and sulfobutylether β-cyclodextrin.

11. The composition of claim 1, wherein the nanocomposite is a gene therapeutic agent.

12. The composition of claim 1, wherein the nanocomposite has a size from about 200 to about 300 nm.

* * * * *